(12) United States Patent
Graff et al.

(10) Patent No.: US 6,931,931 B2
(45) Date of Patent: Aug. 23, 2005

(54) DEVICE FOR ULTRASONIC WELD SEAM TESTING OF LONGITUDINALLY WELDED PIPES FOR LONGITUDINAL AND TRANSVERSAL ERRORS

(75) Inventors: Alfred Graff, Essen (DE); Jürgen Verhoeven, Moers (DE); Thomas Kersting, Mülheim (DE); Ludwig Oesterlein, Ratingen (DE)

(73) Assignee: Mannesmannröhren-Werke AG, Mülheim (DE)

( * ) Notice: Subject to any disclaimer, the term of this patent is extended or adjusted under 35 U.S.C. 154(b) by 33 days.

(21) Appl. No.: 10/482,812

(22) PCT Filed: Jul. 4, 2002

(86) PCT No.: PCT/DE02/02497

§ 371 (c)(1),
(2), (4) Date: Jan. 20, 2004

(87) PCT Pub. No.: WO03/005017

PCT Pub. Date: Jan. 16, 2003

(65) Prior Publication Data

US 2004/0237653 A1 Dec. 2, 2004

(30) Foreign Application Priority Data

Jul. 5, 2001 (DE) .......................................... 101 34 696

(51) Int. Cl.⁷ ................................................. G01N 9/24
(52) U.S. Cl. ..................................................... 73/622
(58) Field of Search ......................... 73/588, 620, 622, 73/624, 625, 850

(56) References Cited

U.S. PATENT DOCUMENTS 4,131,026 A * 12/1978 Ries et al. ..................... 73/625
4,395,911 A * 8/1983 Macecek ........................ 73/622
5,085,082 A * 2/1992 Cantor et al. .................. 73/622

FOREIGN PATENT DOCUMENTS

| DE | 26 07 011 A | 9/1977 |
| DE | 26 55 364 A | 6/1978 |
| DE | 41 13 519 A | 10/1992 |
| DE | 198 26 759 C | 12/1999 |
| GB | 2 012 047 A | 7/1979 |

OTHER PUBLICATIONS

Scott Lebsack and Helmut Heckhauser in the magazine "Materials Evaluation" (Aug. 1995, pp. 886–891), entitled "Immersion Probe Arrays for Rapid Pipeline Weld Inspection".

* cited by examiner

Primary Examiner—Max Noori
(74) Attorney, Agent, or Firm—Henry M. Feiereisen

(57) ABSTRACT

A device for ultrasonic weld seam testing of longitudinally includes two testing carriages swingably suspended and moveable on the pipe surface to the right and left of the weld seam for longitudinal flaw inspection, and one testing carriage swingably suspended in central relationship to the weld seam and moveable on the pipe surface for transverse flaw inspection. Each testing carriage has a mount for accommodating at least one testing head which includes an oscillator, and at least one coupling medium connection having a channel ending in the region of the oscillator and configured as nozzle in the outlet area. The test head for longitudinal flaw inspection can be arranged at various fixed and predefined angle positions at variable distance to the nozzle in the mount, and the test head for transverse flaw inspection can be arranged, together with the mount, at a variable distance to the pipe surface in a support element accommodating the mount.

13 Claims, 11 Drawing Sheets

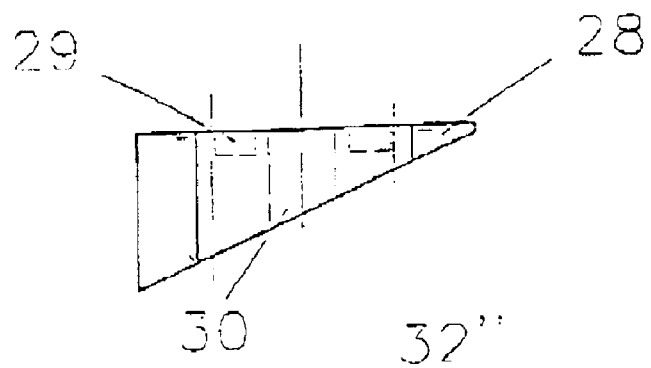
Fig. 6a
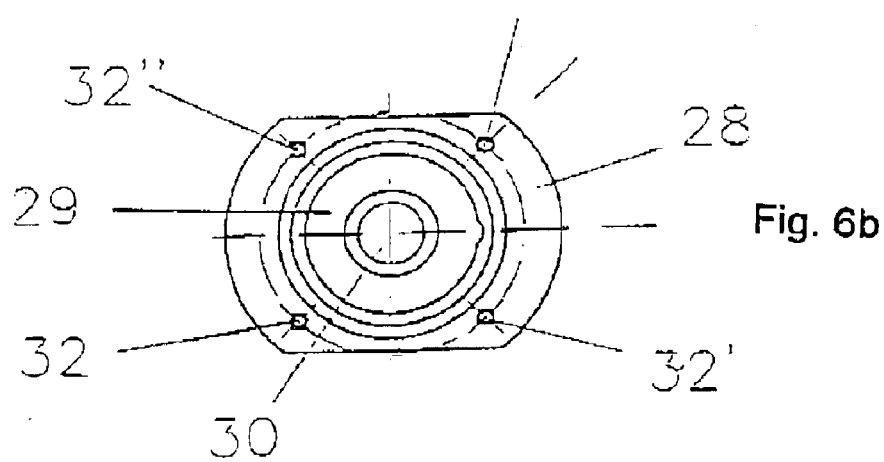
Fig. 6b
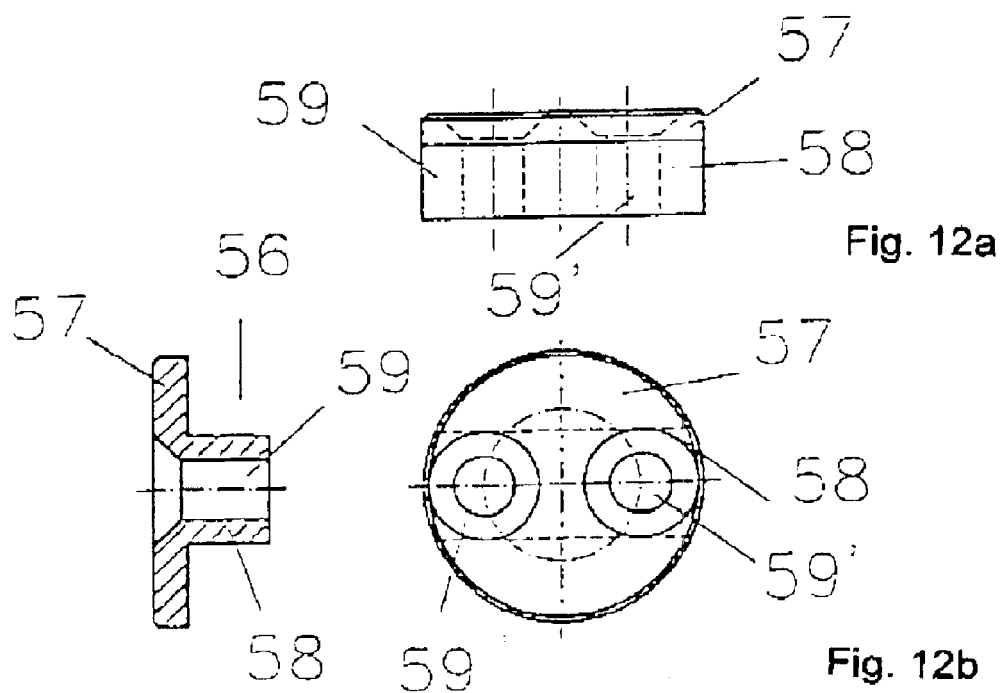
Fig. 12a
Fig. 12b

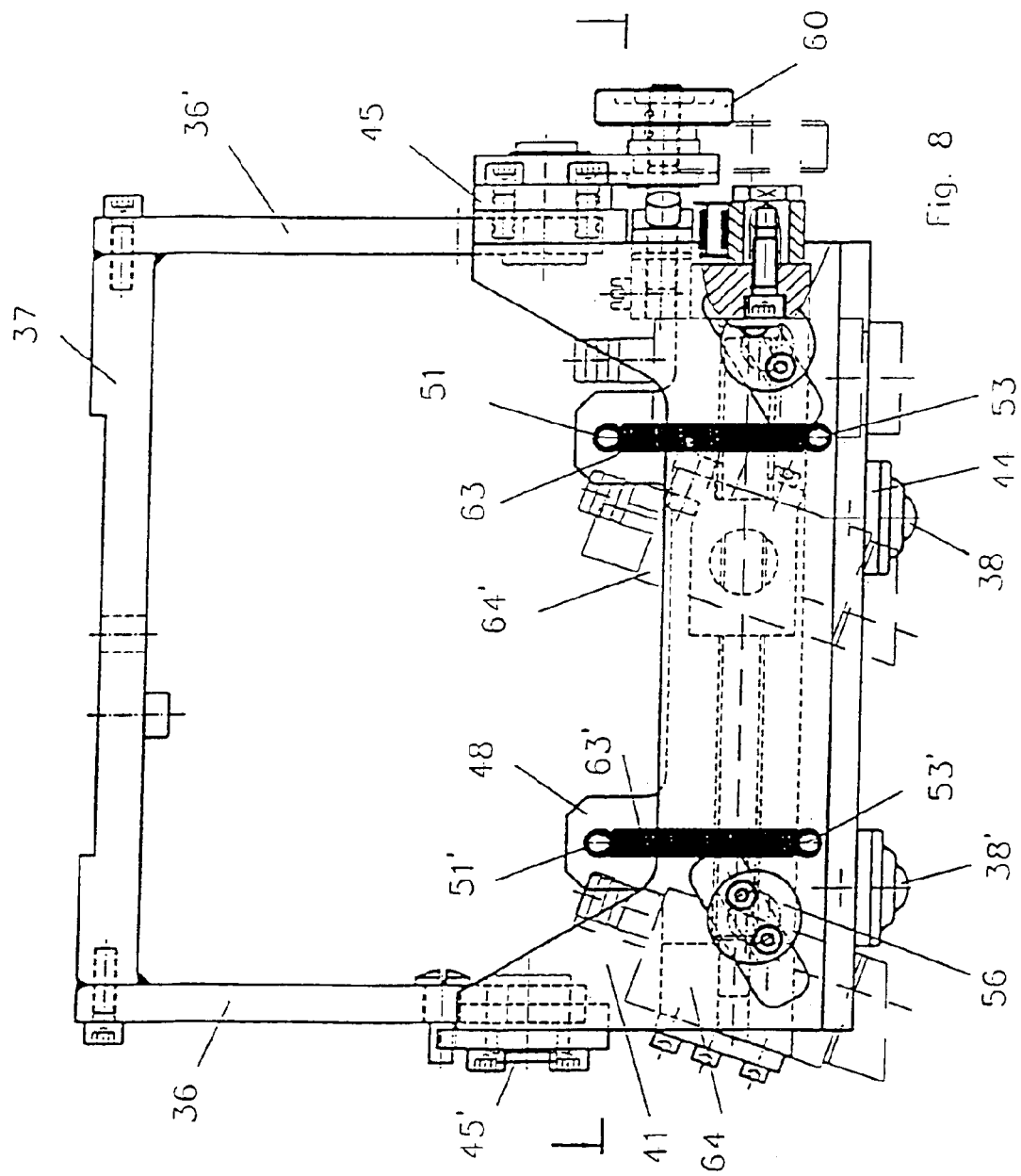

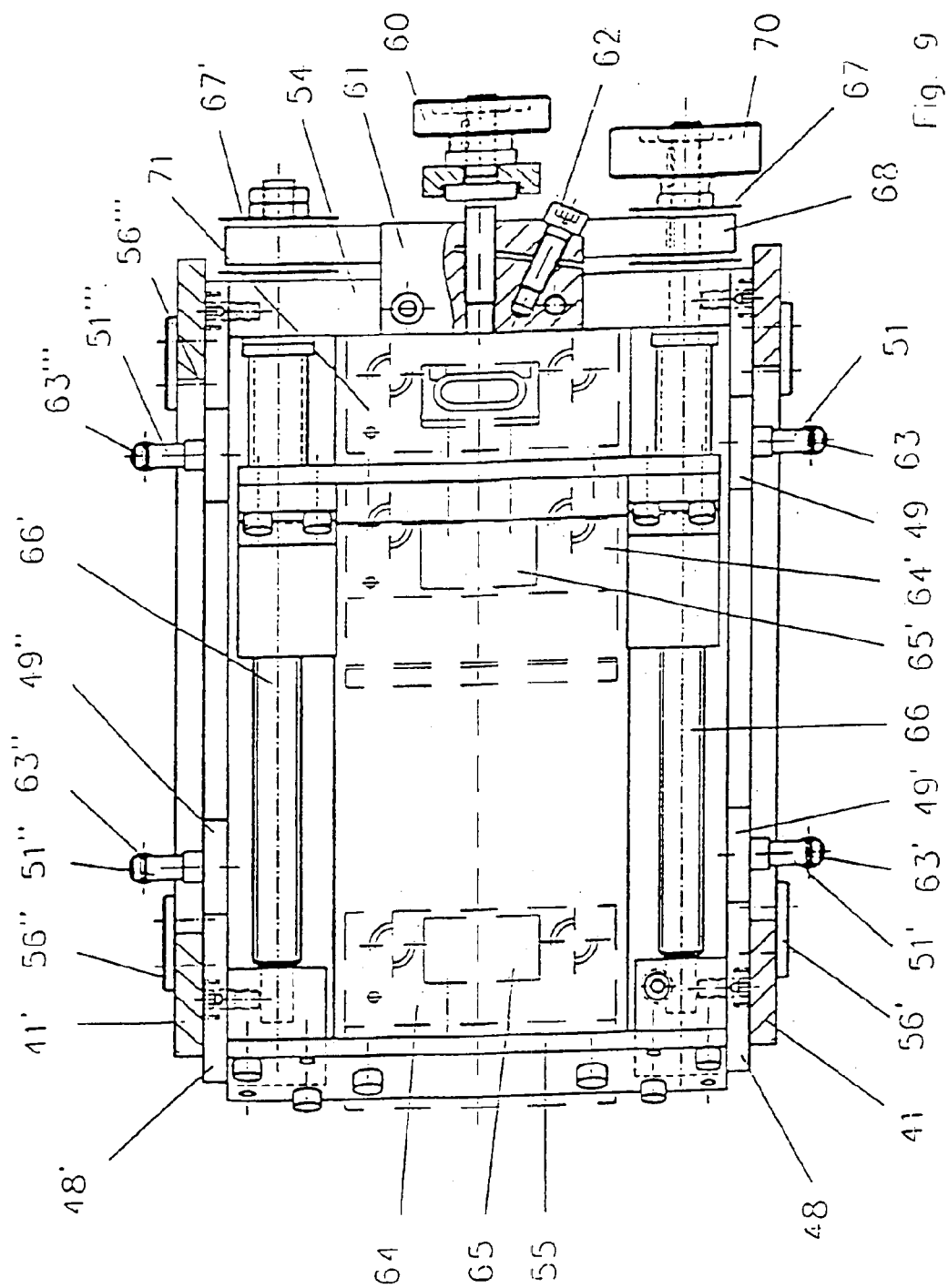

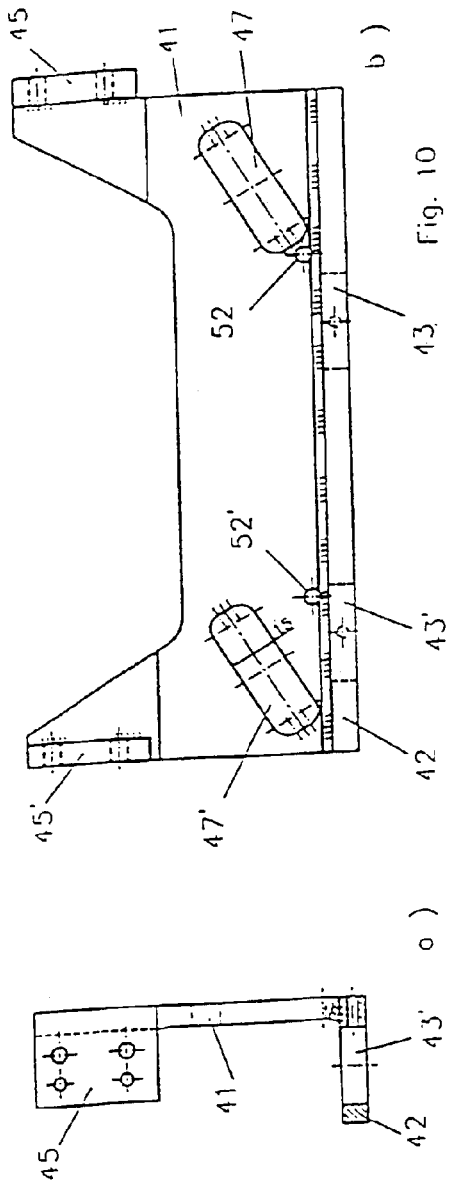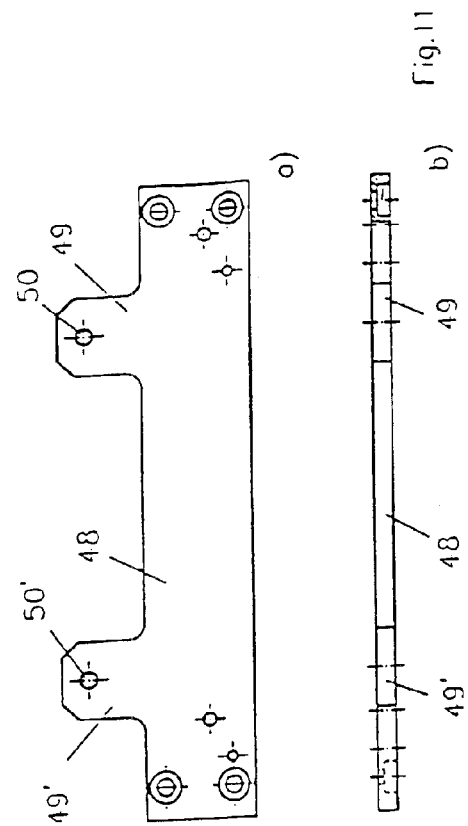

DEVICE FOR ULTRASONIC WELD SEAM TESTING OF LONGITUDINALLY WELDED PIPES FOR LONGITUDINAL AND TRANSVERSAL ERRORS

BACKGROUND OF THE INVENTION

The invention relates to a device for ultrasonic inspection of the weld seam of longitudinally welded pipes—in particular large pipes, for longitudinal and transverse flaws according to the preamble of claim 1.

A device for ultrasonic testing of longitudinal weld seams for longitudinal and transverse flaws has been published by Scott Lebsack and Helmut Heckhauser in the magazine "Materials Evaluation" (August 1995, pages 886–891), entitled "Immersion Probe Arrays for Rapid Pipeline Weld Inspection". Included here is a holding system in which two test head systems are mounted. Each test head system includes four test heads to inspect for longitudinal flaws and a test head to inspect for transverse flaws. The two test head systems for longitudinal flaw inspection are positioned to the right and left next to the weld seam. The test head for transverse flaw inspection extends slantingly at an angle of about 45° in relation to the weld seam. The oscillators in the test heads are round with a diameter of 5 mm. The test head systems operating in immersion technique is provided with connections for the coupling medium.

DE 198 26 759 C1 discloses a device for ultrasonic testing of longitudinal weld seams for transverse flaws. This known device includes at least one test head which is arranged in a holder element and extends in line with the weld seam and which is provided with an oscillator. The test head is provided with at least one coupling medium connection having a channel ending in the area of the oscillator. Disposed in the test head is a broad rectangular oscillator having a width extending transversely to the weld seam. The channel carrying the coupling medium is shaped in the form of a nozzle in the outlet area and has an opening transverse to the weld seam in correspondence to the width of the rectangular oscillator. The outlet zone of the nozzle is adjusted to the weld seam elevation. The respective nozzle element is connected with the housing by means of long screws which traverse the housing accommodating the test head.

The inspection for transverse flaws includes, preferably, two test heads in tandem disposition. The tandem disposition is suited to different thicknesses of the pipe being tested by fixedly securing one test head on a test carriage and arranging the second test head in a manner to be able to move axially in relation thereto.

The conventional devices have the drawback that the adaptation to greatly varying pipe sizes is difficult and complicated to implement and that there are also problems in connection with adjusting the angle of sound incidence in a reproducible manner. Maintenance works involving replacement of damaged parts are also time-consuming.

SUMMARY OF THE INVENTION

It is therefore an object of the invention to provide a device for ultrasonic weld seam testing of longitudinally welded pipes, in particular large pipes, for longitudinal and transverse flaws, which allows a simple adaptation to varying pipe sizes and which ensures a reproducible adjustment of the angle of sound incidence. Maintenance works should be simplified by the novel device.

This object is attained by a device for ultrasonic weld seam testing of longitudinally welded pipes, in particular large pipes, for longitudinal and transverse flaws, which device includes two swingably suspended test carriages which are movable on the surface of the pipe to the right and left next to the weld seam and provided to inspect for longitudinal flaws, and a swingably suspended test carriage which is aligned in the center relative to the weld seam for movement on the surface of the pipe and provided for transverse flaw inspection, wherein each test carriage includes a transducer for accommodating at least one test head which has an oscillator, and at least one coupling medium connection having a channel which ends in the area of the oscillator and is configured in the outlet zone in the form of a nozzle, wherein the respective nozzle element is connected by screws with the transducer, characterized in that the test head for longitudinal flaw inspection can be arranged in different, fixed and predefined angle positions but at variable distance to the nozzle element in the transducer (8) and that the test head(s) for transverse flaw inspection including all the respective transducers are commonly arranged at a variable distance to the pipe surface in a frame accommodating the transducers.

According to the teaching of the invention, the test head for longitudinal flaw inspection can be arranged in different, fixed predefined angle positions but at variable distance to the nozzle element in the mount. Furthermore, the test head(s) for transverse flaw inspection including all the respective mounts are commonly arranged at a variable distance to the pipe surface in a frame which accommodates the transducers.

The proposed arrangement has the advantage that there is a flexibility to provide different angle positions in order to suit different testing tasks while the angle position, once selected, can be securely fixed in a reproducible manner. This can, for example, be realized by forming an exchangeable insert, comprised of two side panels and a connection piece, and providing on the inside of each of the side panels a recess at a certain angular disposition for insertion and securement of the mount for the test head. This ensures that the test head emits acoustic beams in the angular disposition predefined in the recess. The securement of the mount between both side panels is, preferably, realized by means of screws insertable through the sidewall and rotatable into the mount.

In view of the proposed variable distance of the test head from the nozzle element, the gap for the coupling medium, established between the nozzle element and the end surface of the test head, can be modified. This adaptation can be utilized to control the required coupling for a reliable inspection, on the one hand, and to influence the drainage of the coupling medium, on the other hand.

It is proposed in connection with the test carriage for transverse flaw inspection to dispose the respective mount for each test head in a support element, which can be adjusted in height in relation to the surrounding frame. Thus, all test heads arranged in the test carriage for transverse flaw inspection can be commonly placed in a very simple manner at the desired distance to the pipe surface. The need for a complicated adjustment of each individual test head is thus eliminated.

Preferably, the test carriage for transverse flaw inspection includes three test heads. One test head is fixed, a second test head moves axially thereto for transverse flaw inspection, and a third test head is fixed for doubling inspection.

In order to realize the known axial displacement of the second test head, the arrangement of two spindles in the support element is proposed which are each provided at their end surface with a toothed belt disk. When wrapping an endless toothed belt about both toothed belt disks, rotation of one spindle by means of a knurled nut results in a rotation of both spindles to thereby change the axial distance of the second test head in relation to the first test head.

The nozzle elements are exposed to wear as a consequence of their possible contact of the underside with the pipe surface. In order to enable easy replacement, it is proposed to secure them from below to the transducer with screws. By simply lifting off the test carriage, access to the fastening screws is established so that the worn-out nozzle element can simply be replaced.

Generation of disturbance signals can be avoided by making the nozzle elements of wear-resistant plastic, preferably Teflon.

BRIEF DESCRIPTION OF THE DRAWINGS

Further features, advantages and details of the invention are set forth in the following description of an exemplified embodiment illustrated in a drawing:

It is shown in:

FIGS. 1 to 3 front, side and top views of a test carriage according to the invention for longitudinal flaw inspection, FIGS. 4a, b front and top views of a mount for the test head for longitudinal flaw inspection, FIGS. 5a, b side and top views of a side panel, FIGS. 6a, b side and top views of a nozzle element for longitudinal flaw inspection, FIGS. 7 to 9 front, side and top views of a test carriage according to the invention for transverse flaw inspection, FIGS. 10a, b side and front views of a side part of the frame, FIGS. 11a, 11b front and top views of a side part of the support element, FIGS. 12a, b, two views and a section of a guide part, FIGS. 13a, b top and front views of a tandem disposition of two mounts for receiving test heads for transverse flaw inspection, FIG. 14a a front view of a mount for receiving a test head for doubling inspection, FIG. 14b a section of FIG. 14a.

DETAILED DESCRIPTION OF PREFERRED EMBODIMENTS

Figure 1:
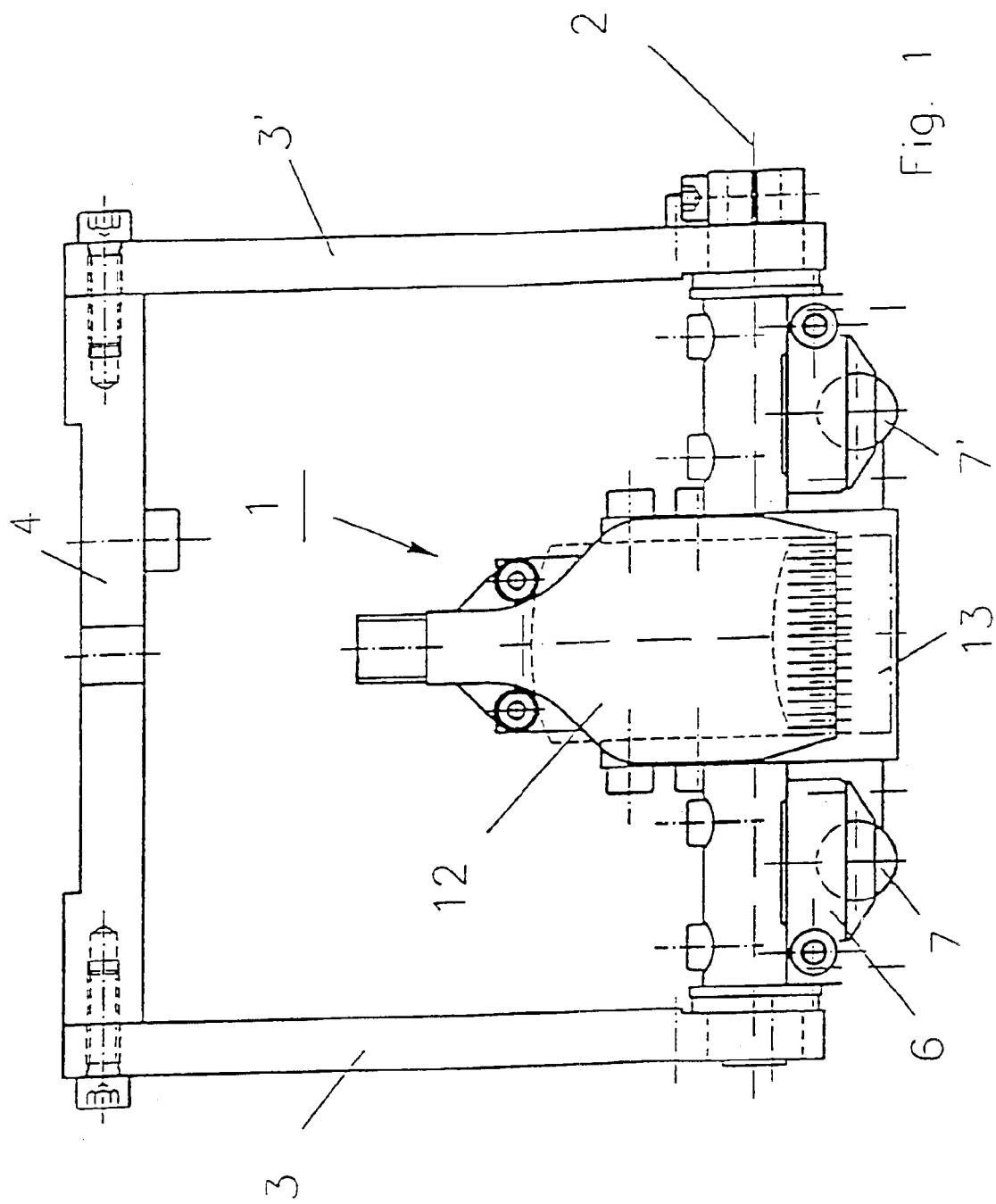
Figure 2:
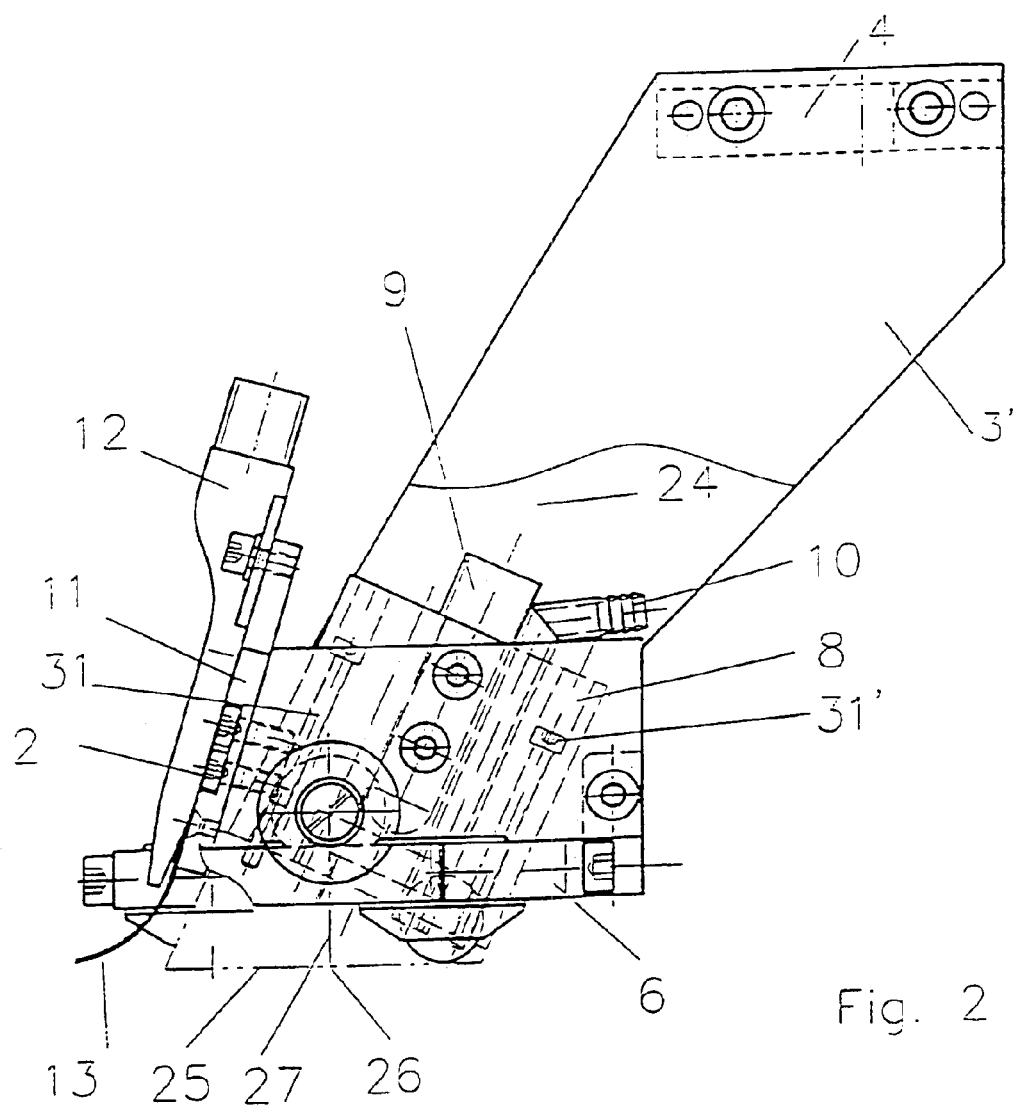
Figure 3:
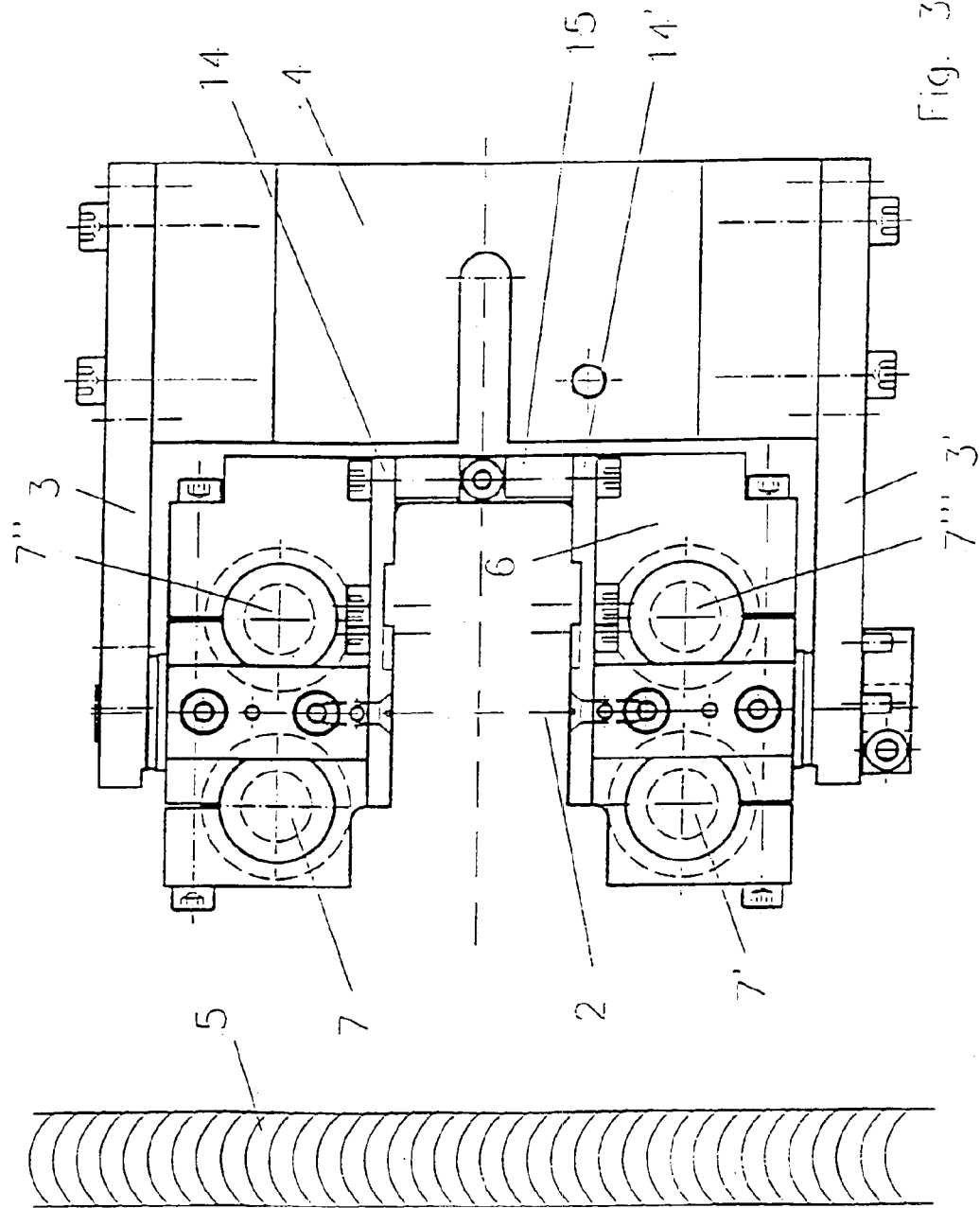

FIGS. 1 to 3 shows front, side and top views of a test carriage according to the invention for longitudinal flaw inspection, whereby the mount 8 (FIG. 4) for receiving a test head has been omitted in the top view (FIG. 3). The test carriage 1 is swingably suspended by means of two side columns 3, 3' and a crossbar 4 interconnecting the side columns 3, 3'.

The position of the longitudinal weld seam 5 to be tested in relation to the test carriage is shown in FIG. 3. For sake of completeness, it should be noted that an analogous test carriage is arranged on the left side of the longitudinal weld seam for longitudinal flaw inspection.

The test carriage 1 is movably arranged on the pipe surface by means of four ball castors 7–7''' clamped in the base plate 6 of the test carriage 1. As will be described in more detail hereinafter, the test carriage 1 includes for the test head 9 a mount 8 (FIG. 4) which can be mounted on the test carriage 1 at a certain predetermined angular disposition. Arranged in the mount 8 is also a nozzle 10 for supply of coupling medium.

In order to prevent an excess flow of coupling medium in the direction of the longitudinal weld seam 5 that may result in signal interferences, a flat jet nozzle 12 and a baffle plate 13 (FIGS. 1, 2) are secured to a plate 11.

Figure 4A:
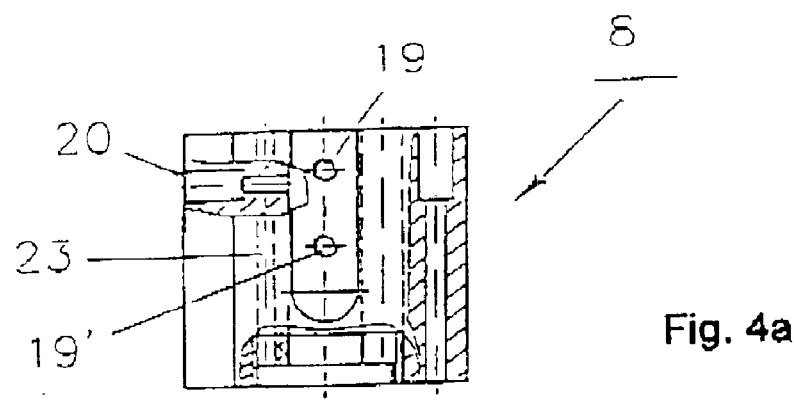
Figure 4B:
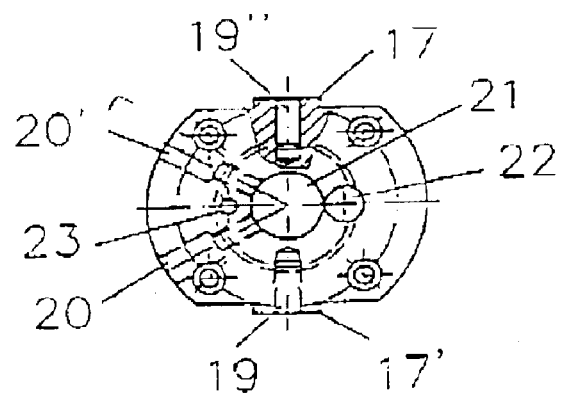
Figure 5A:
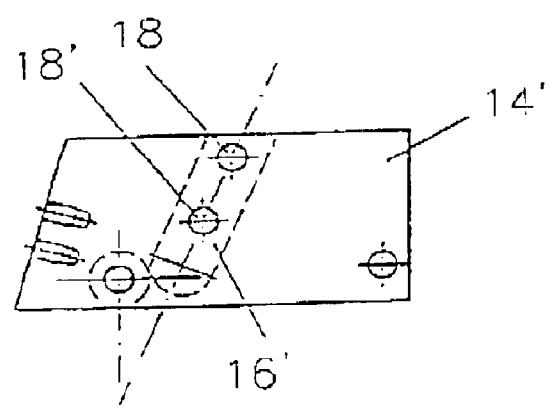
Figure 5B:
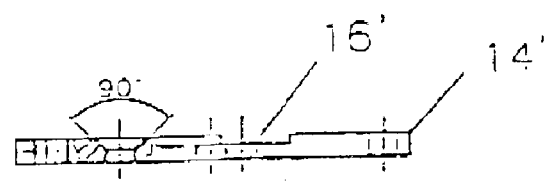

FIG. 3 illustrates in conjunction with FIGS. 4 and 5 the manner by which the mount 8 is secured in the test carriage 1. Hereby two side panels 14, 14' are arranged in opposite disposition in a rectangular opening of the base plate 6 and interconnected by a connection piece 15 to thereby form an exchangeable unitary structure.

According to the illustration in FIG. 5, the side panel 14' is characterized by a slanted recess 16' which is extends on the inside at a certain fixedly predefined angle $\alpha$. This angle $\alpha$ is calculated depending on the desired angle of sound incidence and accordingly milled into the side panel 14' as slanted recess 16'. The different milled side panels 14, 14' define each together with the rigid connection piece 15 an assembly kit for a particular angle of sound incidence.

The mount 8 includes complementary to the recess 16, 16' two nose-like protrusions 17, 17' in opposite relationship so that the mount 8 can be inserted in a simple manner between the side panels 14, 14'. The securement of the mount 8 between both side panels 14, 14' is implemented by means of screws, not shown here, which traverse the side panels 14, 14' and are rotatable into the mount 8. The respective side panel 14' includes hereby two throughbores 18, 18', and the mount 8 includes hereby in the area of each of the nose-like protrusions 17, 17' two threaded bores 19–19'''.

The proposed arrangement has the advantage that a defined angle of sound incidence is established for the test head 8, when an angle $\alpha$ is established for the recess 16, 16' so that the inspection can be constantly carried out with the same predefined angle of sound incidence in a reproducible manner upon use of the assembly kits. The previously typical adjustment of the test head 8 is thus eliminated.

Securement of the test head 9 in the mount 8 is realized by providing a bore 21 in the center of the mount. The actual securement is realized by two, not shown, clamping screws which can be laterally rotated in. The mount 8 includes hereby two lateral threaded bores 20, 20'. The test head 9 can therefore be clamped in the bore 21; is, however, adjustable in height, without altering the angle of sound incidence. In addition to the bore 21 for the test head 9, the mount 8 includes a second smaller bore 22 for arrangement of the nozzle 10. Provided in opposition thereto is a vent bore 23.

The facts relating to the angle of sound incidence will now be described again with reference to the illustration of FIG. 2. As a consequence of the recesses 16, 16', milled in the side panels 15, 15' at a predefined angle $\alpha$, the mount 8 and thus the test head 9 are secured in the test carriage 1 at this angle $\alpha$. By extending the axis 24 of the test head 9, an intersection 26 is established with the horizontal 25. The horizontal 25 is defined by the contact points of the castors 7–7'''. The vertical 27, extending through the pivot axis 2, also extends through said intersection 26. Regardless of the selection of an angle $\alpha$ for the recess 16, 16', it is always assured that the previously explained geometric conditions with respect to the intersection 26 do not change. Only in this case is it possible to maintain a reproducible angle of sound incidence.

FIG. 6 shows the nozzle element 28 which pertains to the mount 8 and is provided for longitudinal flaw inspection. The angular configuration of this nozzle element 28 is suited to the angular configuration of the arrangement of the test head 9. There is, however, no need to provide a same fine-tuned gradation in order to make a specially suited nozzle element 28 for each angle of sound incidence. Rather, it is possible to use a nozzle element 28 for a few angles of sound incidence that are not too far apart. Provided in the nozzle element 28 is a ring channel 29 for overflow of the coupling medium. The drainage hole 30 for the coupling medium is located in the center. The nozzle element 28 is secured by means of four screws 31–31''' (FIG. 2) which extend through bores in the mount 8 and are rotated into the threaded bore 32–32''' of the nozzle element 28. The description of the nozzle element for transverse flaw inspection will further explain the manner in which the type of securement may be modified to achieve a simple exchange capability.

Preferably, the nozzle element 28 is made of Teflon in order to suppress disturbance signals.

Figure 7:
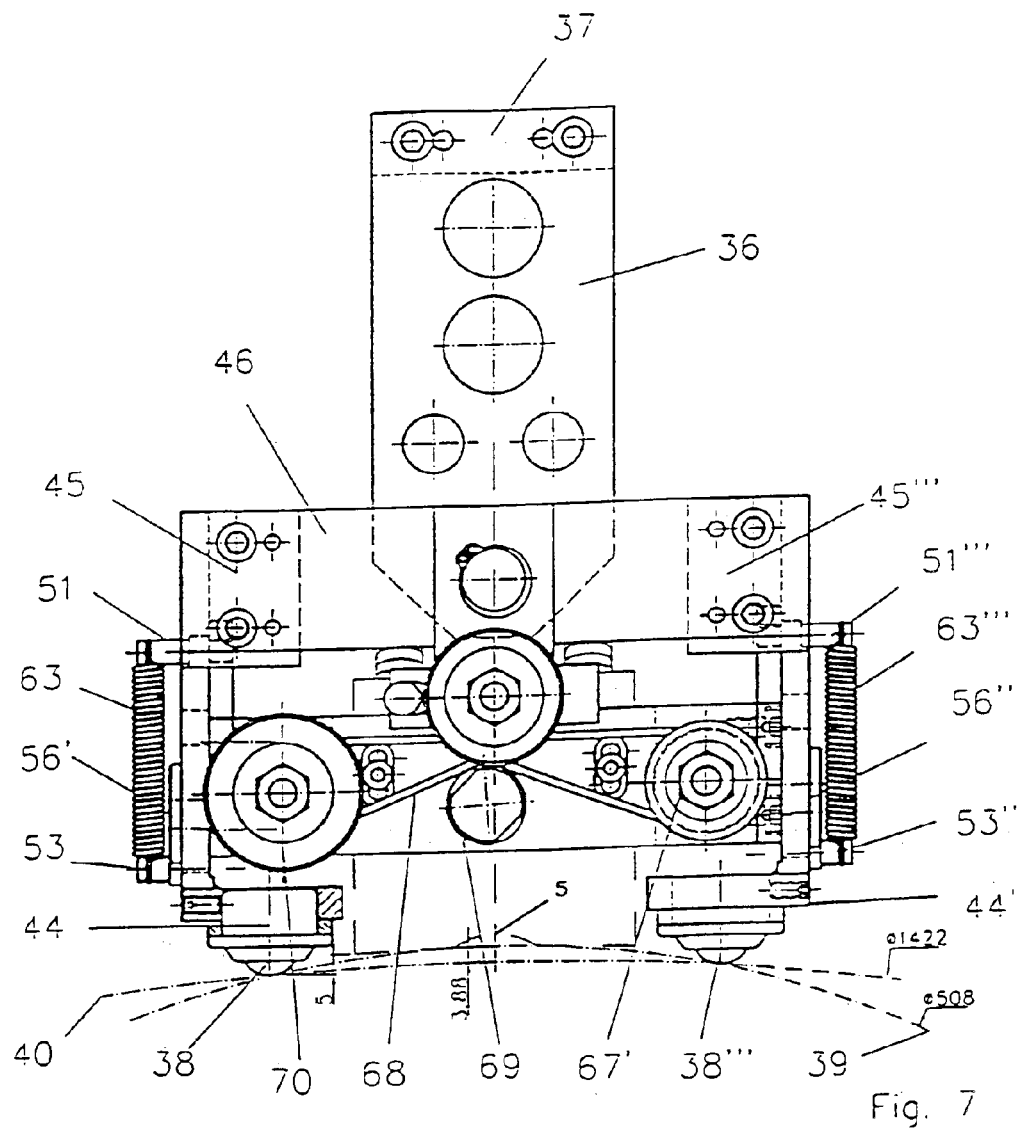

FIGS. 7–9 show front, side and top views of a test carriage 35 according to the invention for transverse flaw inspection. It is also swingably suspended by means of two side columns 36, 36' and a top bar 37. Comparable to the test carriage 1 for longitudinal flaw inspection, also the test carriage 35 for transverse flaw inspection is movably arranged on the pipe surface by means of firmly clamped ball castors 38–38'''.

FIG. 7 depicts the problem relating to the adaptation to different diameters of pipes 39, 40. As can be clearly seen from this example, a height difference of 3.88 mm is to be bridged in the area of the longitudinal weld seam 5, when changing from testing a pipe with an outer diameter of 508 mm to testing a pipe with an outer diameter of 1422 mm. The following description relates to the manner of this adaptation in accordance with the invention.

The test carriage 35 has hereby two side panels 41, 41' (FIGS. 9, 10). The respective side panel 41 is characterized by a horizontal web plate 42 with a bore 43–43''' for receiving the clamping elements 44–44''' for the ball castors 38–38'''. Furthermore, each side panel has welded thereon two vertical web plates 45–45''' which form together with a crossbeam 46, 46' the outer frame of the test carriage 35. Disposed in each of both edge zones of each side panel 41, 41' is a slanted recess 47, 47'.

FIG. 11 shows a side panel 48, 48' of the inner support element. It is provided on the top side with two loop-like webs 49–49'''. These webs 49–49''' have bores 50–50''' for insertion of a stud bolt 51–51'''. In a same manner, also the previously described side panels 41, 41' of the outer frame are provided with bores 52–52''' for insertion of stud bolt 53–53'''. The two side panels 48, 48' of the inner support element are interconnected by two supports 54, 55. The inner support element is vertically adjustably arranged in the outer frame in order to be able to compensate for the different curvature of the pipes to be tested, as described in FIG. 7. The vertical adjustment of the support element in accordance with the invention in relation to the outer frame is realized by means of a guide part 56–56''' (FIG. 12) which includes a collar-like disk 57 and an attached rectangular guide block 58. The guide part 56 is traversed by two bores 59, 59'. The respective guide part 56–56''' is inserted through the recess 47–47''', shown in FIG. 10, and connected with the side panels 48, 48' of the support element by means of screws, not shown here.

By turning a knurled nut 60, an adjustment nut 61 is moved axially (FIG. 9). By means of the support 54, this axial movement of the adjustment nut 61 is transmitted into the entire support element. The guide blocks 58 of the guide parts 56–56''', arranged slantingly in the recesses 47–47''', convert the axial movement of the adjustment nut 61 in a resultant vertical displacement of the support element in relation to the outer frame in accordance with a slant of the recess 47–47'''.

In order to prevent an inadvertent shift during testing, the adjustment nut 61 may be secured in place by means of a clamping screw 62. The inner support element and the outer frame are braced together by springs 63–63''' so that both parts are kept under tension relative to one another.

It is already known in the prior art to move two test heads in tandem configuration for transverse flaw inspection toward one another in axial direction. A mount 64, 64'. connected with the support element, has a rectangular opening 65, 65' for placement of—not shown here—test heads with a rectangular oscillator.

The mount 64, located on the left-hand side in FIG. 9, is fixedly secured on the support 55, while the second mount 64' is axially movable. The axial displacement is implemented by means of two spindles 66, 66'. Arranged on the right-hand end of each spindle 66, 66' is a toothed disk 67, 67'. Wrapped about both toothed disks 67, 67' is an endless toothed belt 68 which can be kept taut by a cam 69 (FIG. 7).

Secured to the toothed disk 67 on the left-hand side of FIG. 7 is a knurled nut 70 to allow movement of the toothed belt 68. A movement of the toothed belt 68 causes both spindles 66, 66' to rotate so that the mount 64' and thus also the test head are moved in axial direction.

In this exemplified embodiment, the test carriage for transverse flaw inspection has arranged therein also a third mount 71 which receives a test head for the doubling inspection and is securely fixed with the support 54. The afore-described height adjustment of the support element results in a common movement of all attached mounts 64, 64' 71 so as to ensure that all three test heads have the same distance to the pipe surface.

Figure 13A:
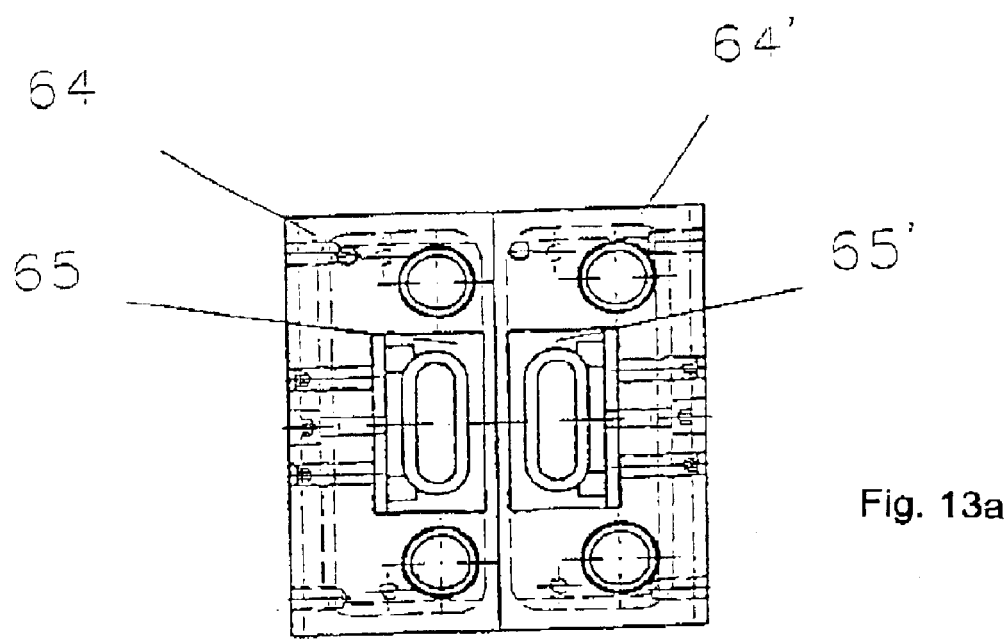
Figure 13B:
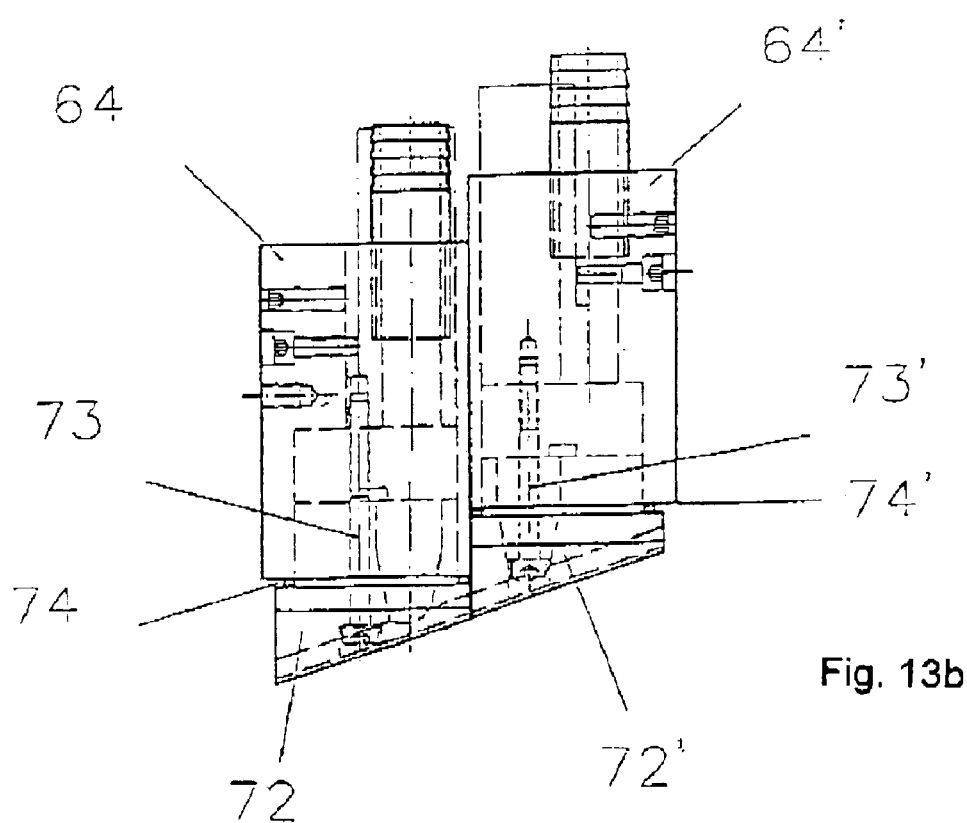

FIG. 13 shows a top view and a front view of two mounts 64, 64' in tandem configuration for receiving test heads for transverse flaw inspection. As this has already been described in detail in the prior art, a more detailed discussion thereof is omitted. However, it should be noted that in accordance with the invention the nozzle elements 72, 72' for the transverse flaw inspection are connected from below by means of screws 73, 73' with the respective mount 64, 64'. The nozzle elements 62, 62' are also made in this exemplified embodiment of Teflon. It may be required to arrange a seal 71, 74' to effect a sealing between nozzle element 72, 72' and mount 64, 64'.

Figures 14A, 14B:
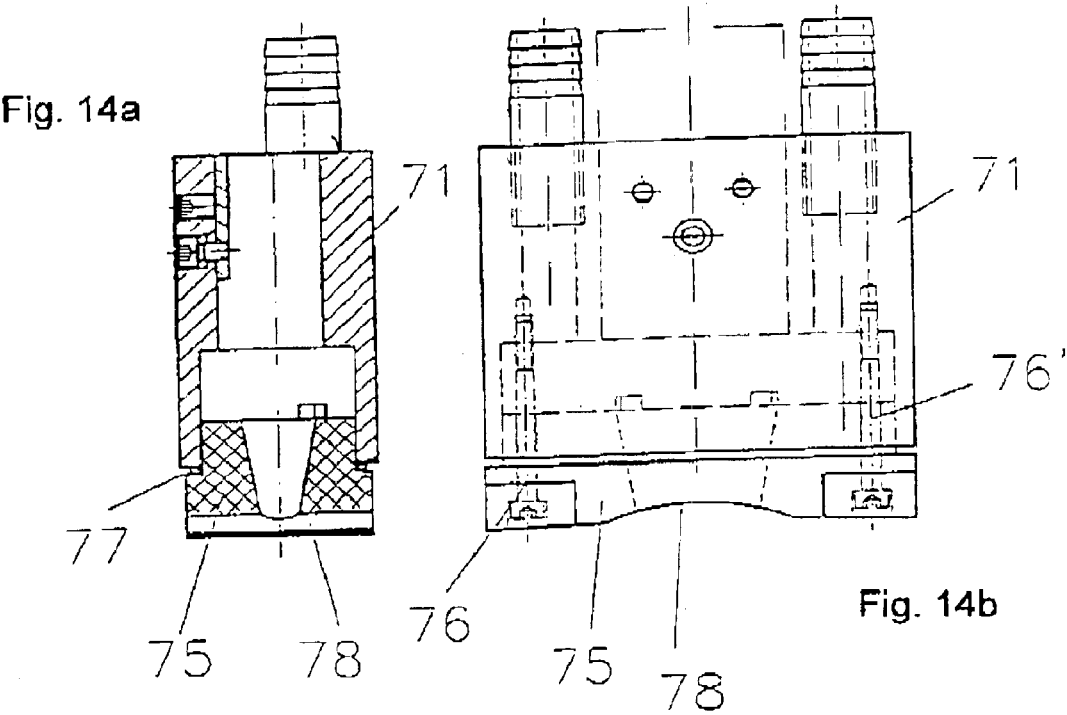

FIG. 14 shows a mount for receiving a test head for doubling inspection. The nozzle element 75 is also connected from below by means of screws 76, 76' with the mount 71. Optionally arranged therebetween is a sealing ring 77. As the mount 71 is placed transversely over the weld seam 5, the nozzle element 75 includes a respectively configured recess 78.

What is claimed is:

1. A device for ultrasonic weld seam testing of a longitudinally welded pipe, in particular a large pipe, for longitudinal and transverse flaws, comprising:

a swingably suspended first test carriage, movable on a surface of a pipe on one side next to a weld seam, for longitudinal flaw inspection; and a swingably suspended second test carriage, disposed in alignment with a center of the weld seam and movable on the surface of the pipe, for transverse flaw inspection, wherein each of the first and second test carriages includes a mount for accommodating at least one test head, which has an oscillator, and at least, one coupling medium connection having a channel which ends in an area of the oscillator and has an outlet zone configured in the form of a nozzle which is secured to the mount, wherein the test head for longitudinal flaw inspection is constructed for arrangement in different, fixed and predefined angle positions at a variable distance to the nozzle in the mount, and wherein the mount for the test head for transverse flaw inspection is arranged at a variable distance to the surface of the pipe in a support element.

2. The device of claim 1, wherein the first test carriage defines a pivot axis and has a base plate, and further comprising two upright side panels which are secured to the base plate in parallel relationship and have each on an inside a recess which extends at an angle, said mount of the first test carriage being provided with two confronting nose-like protrusions which complement the recesses of the side panels for securement between the side panels, wherein the recesses are so angled that an axis of the test head in the mount of the first test carriage extends through an intersection defined by a vertical, which extends through the pivot axis of the test carriage, and a horizontal, which is established by contact points of the test carriage.

3. The device of claim 2, wherein the mount of the first test carriage is secured by at least one screw which is insertable through each side panel and rotatable into the mount.

4. The device of claim 2, further comprising a connection piece for interconnecting the two side panels to form an exchangeable unitary structure.

5. The device of claim 1, further comprising a frame, wherein the support element for holding the mount and the test head is surrounded by and vertically adjustably guided in the frame.

6. The device of claim 5, wherein the support element is connected on each side with two guide parts which are movable in recesses arranged in the frame, and wherein an end surface of the support element is connected with an adjustment nut which interacts with a knurled nut.

7. The device of claim 5, further comprising spring elements for bracing the support element to the frame.

8. The device of claim 1, wherein the second test carriage is provided with three test heads, with a first one of the test heads being fixed, and a second one of the other test heads being movable axially relative to the fixed test head for the transverse flaw inspection, and with a third one of the test head being fixed for doubling inspection.

9. The device of claim 1, wherein the nozzle of each of the test heads is made of wear-resistant plastic.

10. The device of claim 9, wherein the nozzle is made of Teflon.

11. The device of claim 1, wherein the nozzle is secured to the mount by a fastening screw which is insertable from below through the nozzle and rotatable into the mount.

12. The device of claim 8, further comprising a spindle drive for realizing an axial movement of the second test head, said spindle drive including two spindles which are arranged in the support element and which have each an end surface for attachment of a toothed disk which is wrapped around by an endless toothed belt.

13. The device of claim 12, further comprising a knurled nut secured to the toothed disk of one of the spindles.

\* \* \* \* \*

UNITED STATES PATENT AND TRADEMARK OFFICE
CERTIFICATE OF CORRECTION

PATENT NO. : 6,931,931 B2
DATED : August 23, 2005
INVENTOR(S) : Graff et al.

It is certified that error appears in the above-identified patent and that said Letters Patent is hereby corrected as shown below:

<u>Title page,</u>
Item [75], Inventors:
Correct third inventor's city of residence to -- Moers --;
Correct fourth inventor's city of residence to -- Mülheim --.

Signed and Sealed this

Third Day of January, 2006

JON W. DUDAS
*Director of the United States Patent and Trademark Office*